US00PP35831P3

(12) United States Plant Patent
Vicente et al.

(10) Patent No.: US PP35,831 P3
(45) Date of Patent: May 28, 2024

(54) STRAWBERRY PLANT NAMED 'SGS73 1'

(50) Latin Name: ***Fragaria* X *ananassa* Duch.**
Varietal Denomination: SGS73 1

(71) Applicant: INSTITUTO NACIONAL DE INVESTIGACION AGROPECUARIA (INIA), Montevideo (UY)

(72) Inventors: Esteban Vicente, Salto (UY); Ariel Manzzioni, Salto (UY); Joanna Lado, Salto (UY); Matías González, Salto (UY); Ana Arruabarrena, Salto (UY); Mario Giambiasi, Salto (UY)

(73) Assignee: INSTITUTO NACIONAL DE INVESTIGACION AGROPECUARIA, Yakima, WA (US)

( * ) Notice: Subject to any disclaimer, the term of this patent is extended or adjusted under 35 U.S.C. 154(b) by 0 days.

(21) Appl. No.: 17/300,752

(22) Filed: Oct. 19, 2021

(65) Prior Publication Data

US 2022/0151121 P1 May 12, 2022

Related U.S. Application Data

(60) Provisional application No. 63/204,816, filed on Oct. 27, 2020.

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208, 209
CPC ... A01H 5/08; A01H 5/00; A01H 5/02; A01H 6/74; A01H 6/7409
See application file for complete search history.

(56) References Cited

PUBLICATIONS

Vicente et al. El Cultivar de Frutilla 'Inia Yrupe' (SGS73.1), Instituto Nacional de Investigacion Agropecuaria Uruguay Hoja de Divulgacion 2019, No. 109, 4 pp. (Year: 2019).*
Google English translation of Lado et al. 2022, 6 pp. (Year: 2022).*
CPVO Register S2/S3 version 4.10.7 for SGS73 1, retrieved on Aug. 1, 2023 at https://online.plantvarieties.eu/publicConsultationDetails?registerId=20221778&denomination=sgs73%201, 3 pp. (Year: 2023).*

* cited by examiner

*Primary Examiner* — June Hwu
(74) *Attorney, Agent, or Firm* — Svendsen Legal, LLC

(57) ABSTRACT

A new short-day strawberry plant named 'SGS73 1' is disclosed, with exceptional fruit shape and flavor characteristics.

4 Drawing Sheets

CROSS-REFERENCE TO RELATED APPLICATIONS

This application claims priority of provisional application Ser. No. 63/204,816 as filed on Oct. 27, 2020.
Genus and species: *Fragaria* X *ananassa* Duch.
Variety denomination: 'SGS73 1'.

STATEMENT REGARDING FEDERALLY SPONSORED RESEARCH OR DEVELOPMENT

None

BACKGROUND OF THE INVENTION

'SGS73 1' is a product of a controlled breeding program carried out by the joint inventors in Salto, Uruguay. It originated from the cross between two advanced clones carried out in 2013 in Salto, Uruguay. It was selected in the field of individuals in 2014 and later was asexually propagated by rooting stolons, which were planted and evaluated in preliminary and advanced agronomic trials against reference varieties in the Salto area, Uruguay. Simultaneously it was characterized by its sanitary behavior against the natural infection of root/crown, foliar and fruit pathogens (2015-

2019). During 2018, it was evaluated at the productive level in the producer's farm, with a panel made up of producers, technicians, nurserymen, and breeding program staff. The following year, it was validated on a larger scale at four representative commercial farms. During the last three years their physical, chemical, and postharvest life quality of fruit has been characterized. In 2019, the cultivar was registered, protected, and licensed.

Contrast is made with maternal parent 'SGN48.3' (INIA Ágata™), in which 'SGS73 1' is more tolerant to stem and root diseases with superior fruit quality and agronomic behavior. According to the information available, 'SGS73 1' would be recommended for autumn, winter, and spring production in protected cultivation in the northwest region of Uruguay. In a semi-early productivity comparison to 'SGN48.3' (with harvests in August and September in Salto, Uruguay); 'SGS73 1' exhibits a faster vegetative development and ease of harvest; better fruit quality, especially in shape and flavor; and health, due to lower incidence of botrytis, spider mites and powdery mildew in the 'SGS73 1' fruit.

Paternal parent is 'SGP20.2', is proprietary and has not yet been commercialized. By comparison, 'SGS73 1' produces fruit earlier in the season, and the fruit of 'SGS73 1' is typically larger than that of 'SGP20.2'.

BRIEF DESCRIPTION OF THE PHOTOGRAPHS

Figure 1:
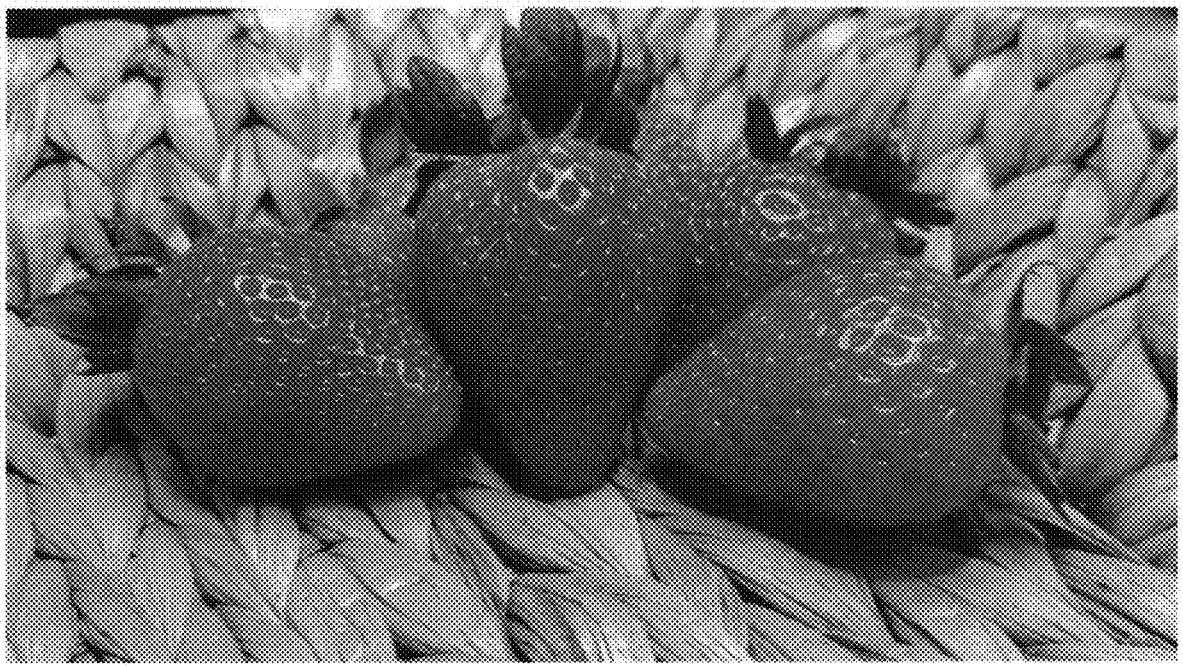
FIG. 1 illustrates the fruit of 'SGS73 1' harvested August 2019 from a 5-month-old plant.
Figure 2:
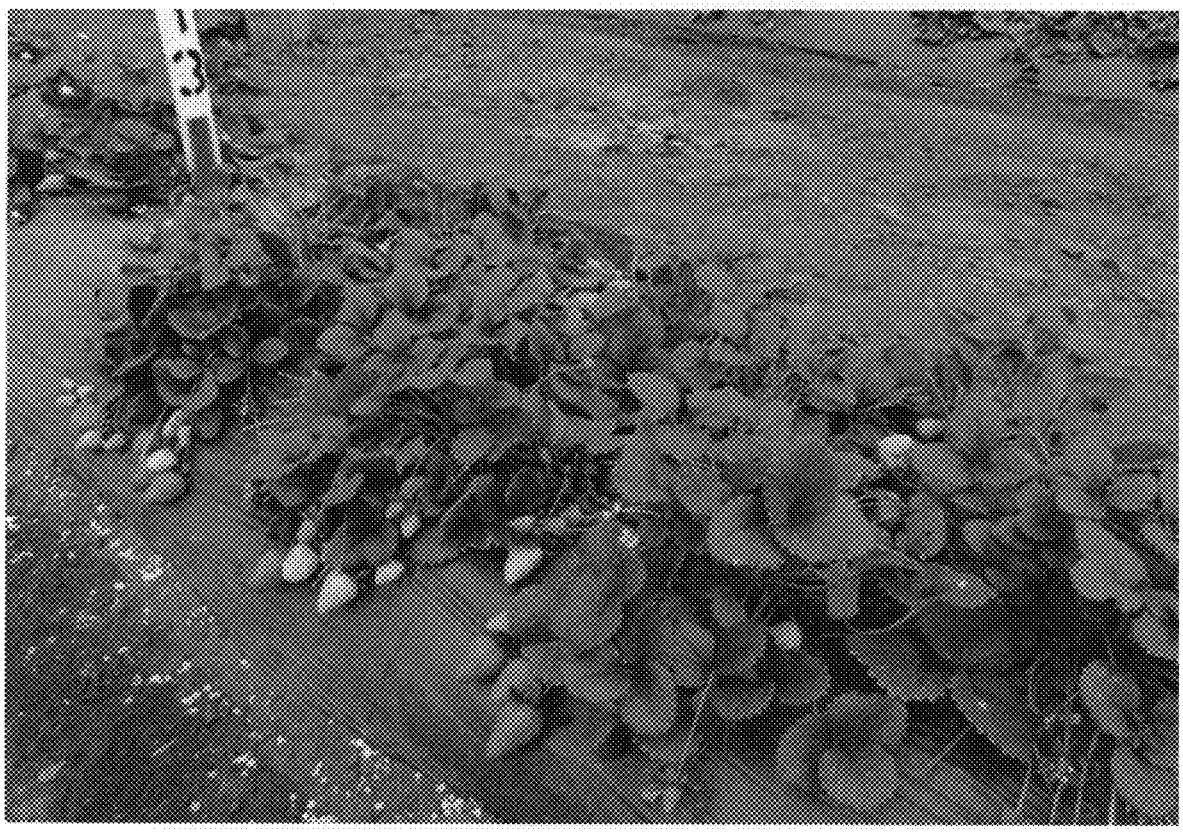
FIG. 2 illustrates plants of 'SGS73 1' at 6 months of age cultivated with black plastic mulch and drip irrigation.
Figure 3:
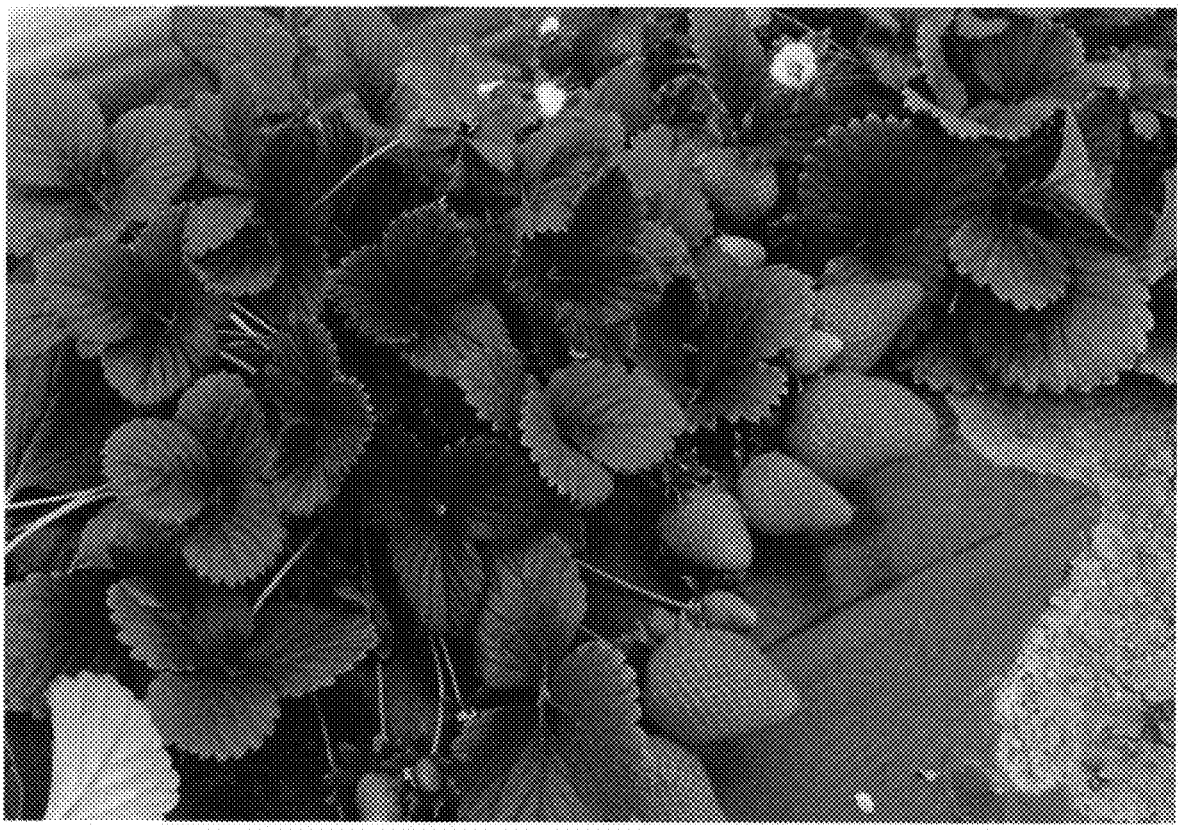
FIG. 3 illustrates plants of 'SGS73 1' at 5 months of age cultivated with black plastic mulch and drip irrigation.
Figure 4:
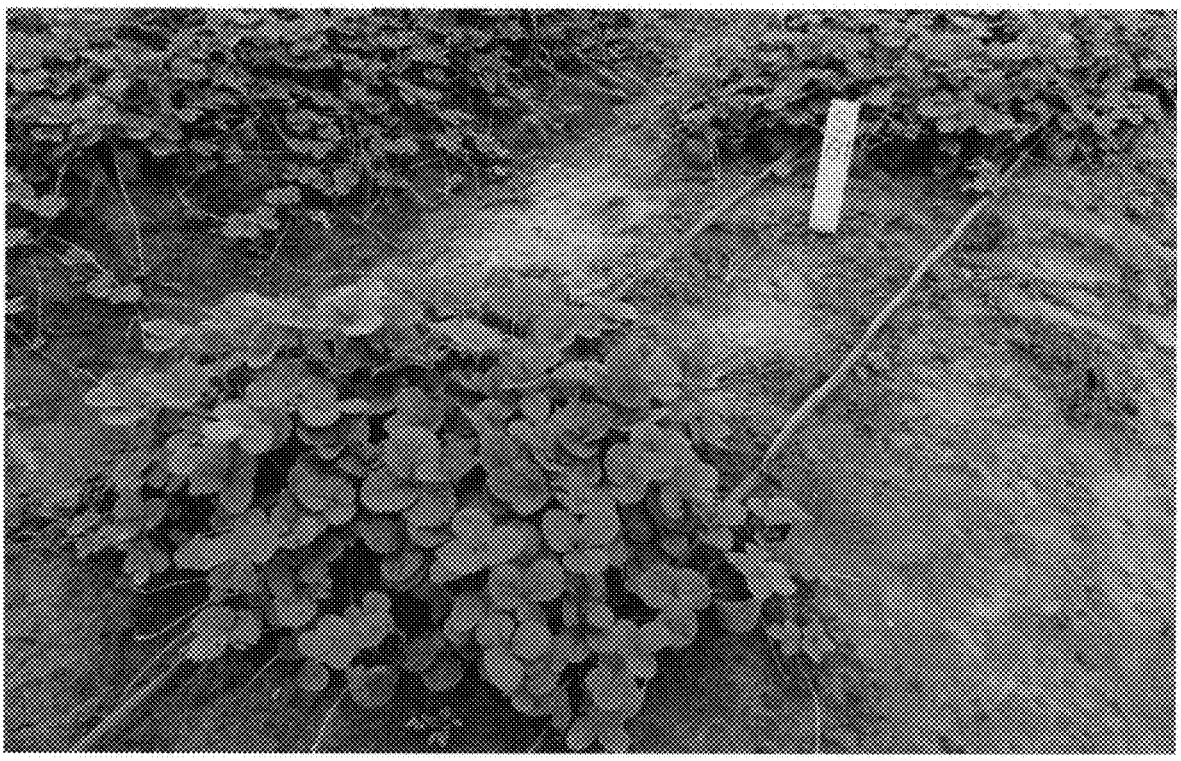
FIG. 4 illustrates greenhouse 'SGS73 1' 4-month-old mother plants after transplantation and planted in pots with 20 days of rooting.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2019 growing seasons in Salto Grande, Salto, Uruguay. It should be understood that the characteristics described will vary somewhat depending upon cultural practices and climatic conditions and can vary with location and season. Quantified measurements are expressed as an average of measurements taken from a number of individual plants of the new variety. The measurements of any individual plant or any group of plants, of the new variety may vary from the stated average. The below listed color terminology follows The R.H.S. Large Colour Chart, Sixth Revised Edition (2015;2019 Reprinted ED.).

General description:

*Ploidy*.—Octoploid.

*Blooming period*.—April thru November in the Southern Hemisphere.

*Plant type*.—Not remontant. Short day. Early fruiting short-day types as it produces fruit earlier in the season.

*Plant habit*.—Erect.

*Root description*.—Moderately branching; medium-high density. Medium-high in thickness, fibrous; typically, cream white to white in color.

*Propagation*.—By runners, cuttings, and direct rooting in pots.

*Growth rate*.—Medium-high vigor.

*Stolons*.—

*Stolon description*.—Number of stolons: few; anthocyanin coloration: weak; density of pubescence: medium.

*Stolon average length*.—26.4 mm.

*Stolon color designation*.—Yellow-Green Group 145, Strong Yellow Green A.

Foliage description:

*Leaf division*.—Compound with typically three leaflets per leaf.

*Leaf average size*.—199×127 mm.

*Leaf blistering*.—Medium.

*Leaf glossiness*.—Medium.

*Leaf variegation*.—Absent.

*Leaf arrangement*.—Typical spiral arrangement.

*Terminal leaf size*.—121×94 mm.

*Leaflet shape in cross section*.—Concave.

*Leaflet length in relation to width*.—Equal.

*Leaflet margins*.—Crenate.

*Leaflet base*.—Obtuse to rounded.

*Leaflet apex*.—Rounded.

*Leaflet venation*.—Pinnate.

*Upper leaflet color*.—Green Group 137, Moderate Olive Green B.

*Lower leaflet color*.—Green Group 138, Moderate Yellow Green B.

*Petiole*.—Length medium: 10 cm to 15 cm; Diameter: about 3 mm to 4.5 mm; attitude of hairs: slightly outwards; density of pubescence: sparse.

*Petiole color designation*.—Yellow-Green Group 146, Moderate Yellow Green C.

*Petiolules*.—Length 0.5 cm to 0.8 cm.

*Petiolules color designation*.—Yellow-Green Group 146, Moderate Yellow Green C.

*Stipule*.—Anthocyanin coloration medium.

*Stipules color designation*.—Orange-Red Group 35, Strong Yellowish Pink C.

Flower description:

*Position of inflorescence in relation to foliage*.—Same level.

*Flower initiation and expression conditions*.—Very low to no cold requirements to flower, very early variety with a short day.

*Time of flowering* (50% *of plants at first flower*).—Very early; in Uruguay commercial strawberry varieties typically bloom from April to November.

*Pedicel average size*.—90.0 mm.

*Corolla average size*.—29.0×25 mm.

*Calyx size in relation to corolla*.—Larger.

*Calyx position on fruit*.—Inserted.

*Diameter of calyx*.—1 cm to 2 cm.

*Petals*.—Length in relation to width: moderately longer; color of upper side: White Group NN155, White C; length: 8 mm to 12 mm; width: 8 mm to 10 mm.

*Petal arrangement*.—Free.

*Peduncle*.—8 cm to 12 cm.

*Peduncle color designation*.—Yellow-Green Group 145, Strong Yellow Green A.

*Pistils*.—Quantity per flower: about 28 to 32.

*Stigma*.—Shape rounded.

*Stamens*.—Quantity per flower: about 20 to 30.

Fruit description:

*Shape*.—Conical-cordiform.

*Season of harvest*.—July to September.

*Time of ripening* (50% *of plants with first ripe fruit*) .—Very early; in Uruguay the harvest begins in Mid-May.

*Time of bearing*.—20 to 25 days depending on weather condition and season of the year.

*Hardiness*.—Observed Plant Hardiness Zone 9b.

*Size*.—63×38 mm (Large).

*Evenness of surface*.—Even or very slightly uneven.

*Attitude of sepals on fruit*.—Upwards.

*Sepals color designations*.—Upper sepal (mature): Green Group 137, Moderate Olive Green B; Lower sepal (mature): Green Group 138, Moderate Yellow Green B.

*Glossiness*.—High gloss, outstanding fruit appearance.

*External color* (*skin*).—

TABLE 1

| External Color | | | | |
|---|---|---|---|---|
| L* | a* | b* | Hue | Chroma |
| 32.8-38.7 | 32.0-35.2 | 21.5-25.8 | 32.4-36.2 | 39.7-43.7 |

Per CIE 1976 L*a*b* color space (International Commission on Illumination (CIE).

*Internal color*.—

TABLE 2

| Internal Color | | | | |
|---|---|---|---|---|
| L* | a* | b* | Hue | Chroma |
| 58.1-62.3 | 16.3-19.4 | 24.5-27.6 | 53.2-57.8 | 30.3-33.2 |

Per CIE 1976 L*a*b* color space (International Commission on Illumination (CIE).

*Evenness of color of skin*.—Even distribution.
*Color of the fruit core*.—Orange-Red Group N34, Strong Reddish Orange B.
*Acidity*.—0.58% average.
*Sweetness*.—5.50-8.80 brix.
*Firmness*.—Average of 1.12 kg/cm2 (measured with a penetrometer).
*Fruit weight*.—16 g-25 g.
*Shelf life and shipping*.—Average shelf life, 4 days, due to high % bruising (37.5%) on the 5th day, after refrigeration at 2-4° C. With these values, it would be appropriate for the national market and for export markets that do not require many days of travel.
*Market use*.—Primarily fresh market.
*General productivity*.—Good to above average.
*Achene*.—Level with surface; Width of band without achenes: absent or very narrow.

Disease and pest resistance:
*Global response to the disease complex root and stem*.—High-medium field tolerance.
*Resistance to powdery mildew at leaf level*.—Very high.
*Resistance to powdery mildew at fruit level*.—High.
*Resistance to botrytis*.—Low incidence.
*Resistance to spider mites*.—Low preference.
*Resistance to anthracnose in fruit*.—Intermediate.

The invention claimed is:

1. A new and distinct variety of strawberry plant named 'SGS73 1', substantially as illustrated and described herein.

* * * * *